(12) United States Patent
Izuhara et al.

(10) Patent No.: US 7,360,949 B2
(45) Date of Patent: Apr. 22, 2008

(54) RADIOGRAPHY SYSTEM AND TRANSFER BOARD MOVING APPARATUS

(75) Inventors: Akira Izuhara, Tokyo (JP); Toshiyuki Iyama, Tokyo (JP); Kazuhiko Hayakawa, Tokyo (JP); Masashi Maida, Tokyo (JP); Takaya Sato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/485,573

(22) Filed: Jul. 12, 2006

(65) Prior Publication Data

US 2007/0025526 A1 Feb. 1, 2007

(30) Foreign Application Priority Data

Jul. 14, 2005 (JP) .............................. 2005-205490
Dec. 15, 2005 (JP) .............................. 2005-362257

(51) Int. Cl.
*A61B 6/04* (2006.01)
(52) U.S. Cl. .............................. 378/209; 378/20; 5/601
(58) Field of Classification Search .................. 378/20, 378/204, 205, 208, 209; 5/601
See application file for complete search history.

(56) References Cited

U.S. PATENT DOCUMENTS 3,216,049 A * 11/1965 Nevison ........................ 16/44

| 4,105,923 A | 8/1978 | Hynes, Jr. |
|---|---|---|
| 4,914,682 A | 4/1990 | Blumenthal |
| 5,475,884 A | 12/1995 | Kirmse et al. |
| 7,024,710 B2 | 4/2006 | Izuhara |
| 7,131,769 B2 * | 11/2006 | Vezina ........................ 378/209 |
| 2004/0001571 A1 | 1/2004 | Jahrling |
| 2004/0141591 A1 | 7/2004 | Izuhara |
| 2006/0058639 A1 | 3/2006 | Izuhara et al. |
| 2006/0104422 A1 | 5/2006 | Iisaku et al. |
| 2006/0120515 A1 | 6/2006 | Ariyama et al. |

FOREIGN PATENT DOCUMENTS

| DE | 19701346 A1 | 7/1998 |
|---|---|---|
| DE | 19702829 A1 | 7/1998 |
| DE | 10215987 A1 | 11/2003 |
| JP | 2004-173756 | 6/2004 |

OTHER PUBLICATIONS

European Search Report, dated Mar. 19, 2007 (10 pgs.); Applicant: GE Medical Systems Global Technology Company, LLC; Application No. EP06253541.

* cited by examiner

*Primary Examiner*—Jurie Yun
(74) *Attorney, Agent, or Firm*—Armstrong Teasdale LLP

(57) ABSTRACT

The present invention is intended to readily move a transfer board from a stretcher to a radiographic table and to efficiently achieve radiography. The transfer board moved from the stretcher is borne by an intermediate table. The transfer board borne by the intermediate table is moved to the radiographic table by an intermediate table mover, and then borne by the radiographic table.

16 Claims, 12 Drawing Sheets

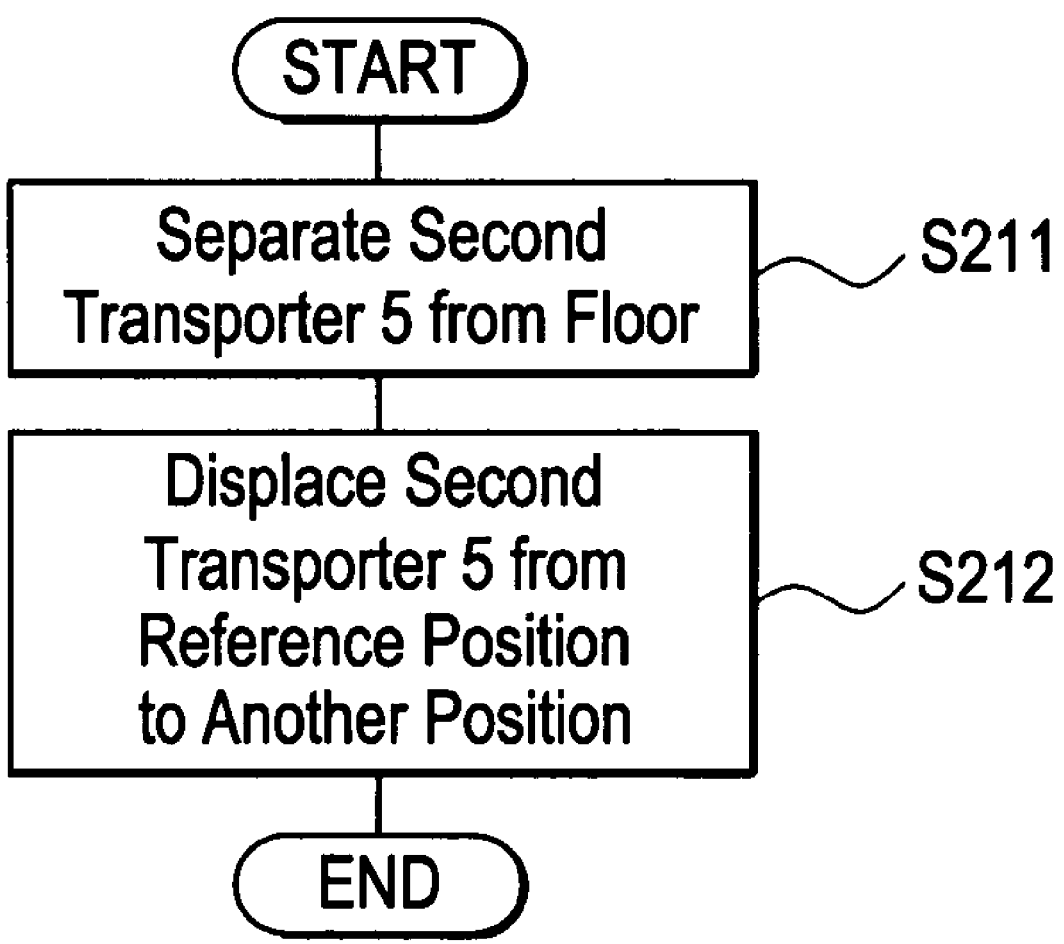

RADIOGRAPHY SYSTEM AND TRANSFER BOARD MOVING APPARATUS

CROSS REFERENCE TO RELATED APPLICATIONS

This application claims the benefit of Japanese Application No. 2005-205490 filed Jul. 14, 2005 and Japanese Application No. 2005-362257 filed Dec. 15, 2005.

BACKGROUND OF THE INVENTION

The present invention relates to a radiography system and a transfer board moving apparatus. More particularly, the present invention is concerned with a radiography system and a transfer board moving apparatus that move a transfer board, which is included in a stretcher and on which a subject lies down, to a radiographic table.

Radiography systems including an X-ray computed tomography (CT) system acquire raw data by scanning a subject lying down in a radiographic space, and produce an image of the subject according to the raw data.

For example, in the X-ray CT system, an X-ray tube and an X-ray detector are incorporated in a scanner gantry so that they will sandwich a radiographic space. A transporter transports a subject borne by a radiographic table to the radiographic space. The X-ray tube irradiates X-rays to the subject while rotating about the subject who is borne by the radiographic table in the radiographic space. The X-ray detector detects X-rays that transmits the subject so as to obtain raw data. Based on the obtained raw data, a tomographic image expressing a subject's plane is produced (refer to Patent Document 1).

[Patent Document 1] Japanese Unexamined Patent Application Publication No. 2004-173756

When an X-ray CT system is used to radiograph a subject, a stretcher is used to transport the subject from outside to a scan room where the X-ray CT system is installed. The stretcher is, for example, a transporter including a transfer board on which a subject lies down and a cart that bears the transfer board so that the transfer board can be dismounted from the cart. When a subject is loaded on a radiographic table included in the X-ray CT system, after the transfer board on which the subject lies down is dismounted from the cart, the transfer board is moved to the radiographic table.

The stretcher is used especially in case of emergency. Therefore, the stretcher is requested to be designed so that the transfer board can be readily moved to the radiographic table in order to facilitate efficient radiography.

In radiography systems including an X-ray CT system, all components including a scanner gantry and a transporter should be accurately disposed at predetermined reference positions. A heavy component is moved and positioned so that an edge of the component will be aligned with a straight line drawn on a floor using, for example, laser light, whereby the components are linearly and relatively disposed in place.

In the work of disposing the components, since adjustment is not easy to do, there is difficulty in improving work efficiency.

In particular, when maintenance is performed in order to, for example, replace a slip ring incorporated in a scanner gantry of an X-ray CT system with a new one, a cover shielding the interior of the scanner gantry must be removed. The components of the X-ray CT system are therefore required to be displaced. For this reason, after the maintenance is completed, the displaced components must be accurately aligned and disposed in place. There is therefore difficulty in improving maintainability. Consequently, a drawback that work efficiency deteriorates becomes obvious.

As mentioned above, radiography systems including an X-ray CT system are requested to improve the efficiency in maintenance and installation work while efficiently achieving radiography.

SUMMARY OF THE INVENTION

Therefore, an object of the present invention is to provide a radiography system and a transfer board moving apparatus capable of improving the efficiency in maintenance and installation work while efficiently achieving radiography.

In order to accomplish the above object, a radiography system in accordance with the present invention includes a radiographic table to which a transfer board on which a subject lies down is moved from a stretcher and which bears the moved transfer board, and a scanner that scans the subject, who lies down on the transfer board borne by the radiographic table, so as to obtain raw data of the subject. The radiography system produces an image of the subject on the basis of the raw data obtained by the scanner. The radiography system further includes an intermediate table that bears the transfer board moved from the stretcher, and a transfer board mover that moves the transfer board, which is borne by the intermediate table, to the radiographic table so that the transfer board will be borne by the radiographic table.

In order to accomplish the aforesaid object, a transfer board moving apparatus in accordance with the present invention moves a transfer board, on which a subject lies down, from a stretcher to a radiographic table. The transfer board moving apparatus includes an intermediate table that bears the transfer board moved from the stretcher, and a transfer board mover that moves the transfer board, which is borne by the intermediate table, to the radiographic table so that the transfer board will be borne by the radiographic table.

In order to accomplish the aforesaid object, a transfer board moving apparatus in accordance with the present invention moves a transfer board, on which a subject lies down, from a stretcher to a radiographic table on which the subject lying down on the moved transfer board is scanned by a scanner. The transfer board moving apparatus includes a transfer board moving apparatus body that moves the transfer board, which is moved from the stretcher, to the radiographic table, caster members that bear the transfer board moving apparatus body, and a body mover that is included in the transfer board moving apparatus body and moves the transfer board moving apparatus body vertically to the caster members.

In order to accomplish the aforesaid object, a radiography system in accordance with the present invention radiographs a subject, and includes a component, caster members that bear the component, and a component mover that is included in the component and moves the component vertically to the caster members.

According to the present invention, there is provided a radiography system and a transfer board moving apparatus capable of improving the efficiency in maintenance and installation work while efficiently achieving radiography.

Further objects and advantages of the present invention will be apparent from the following description of the preferred embodiments of the invention as illustrated in the accompanying drawings.

BRIEF DESCRIPTION OF THE DRAWINGS

FIG. 14 is a flowchart describing actions to be performed when the second transporter 5 is displaced from an installed position according to the second embodiment of the present invention.

DETAILED DESCRIPTION OF THE INVENTION

Embodiments of the present invention will be described below.

First Embodiment

Figure 1:
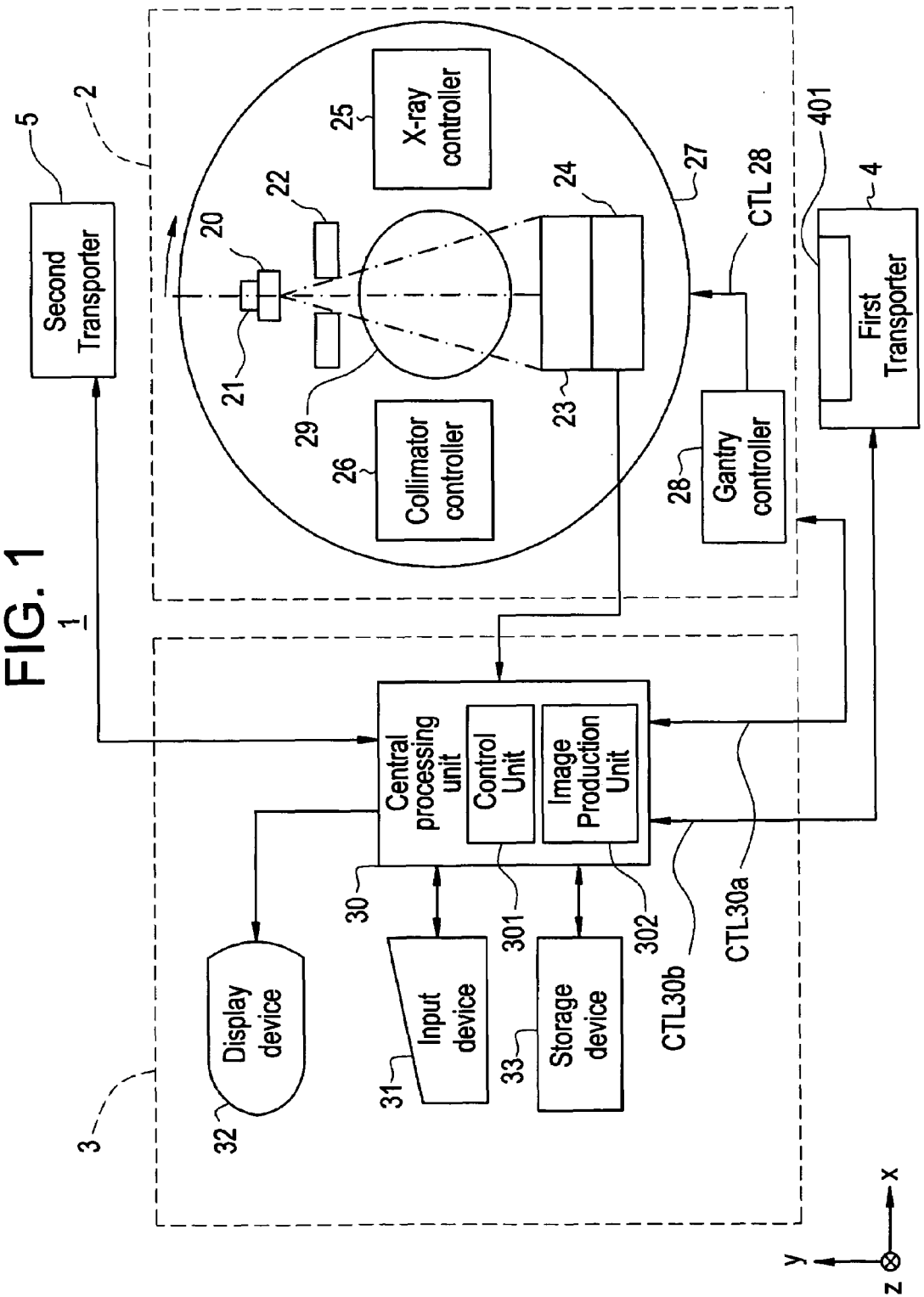
FIG. 1 is a block diagram showing the overall configuration of an X-ray CT system in accordance with the first embodiment of the present invention.
Figure 2:
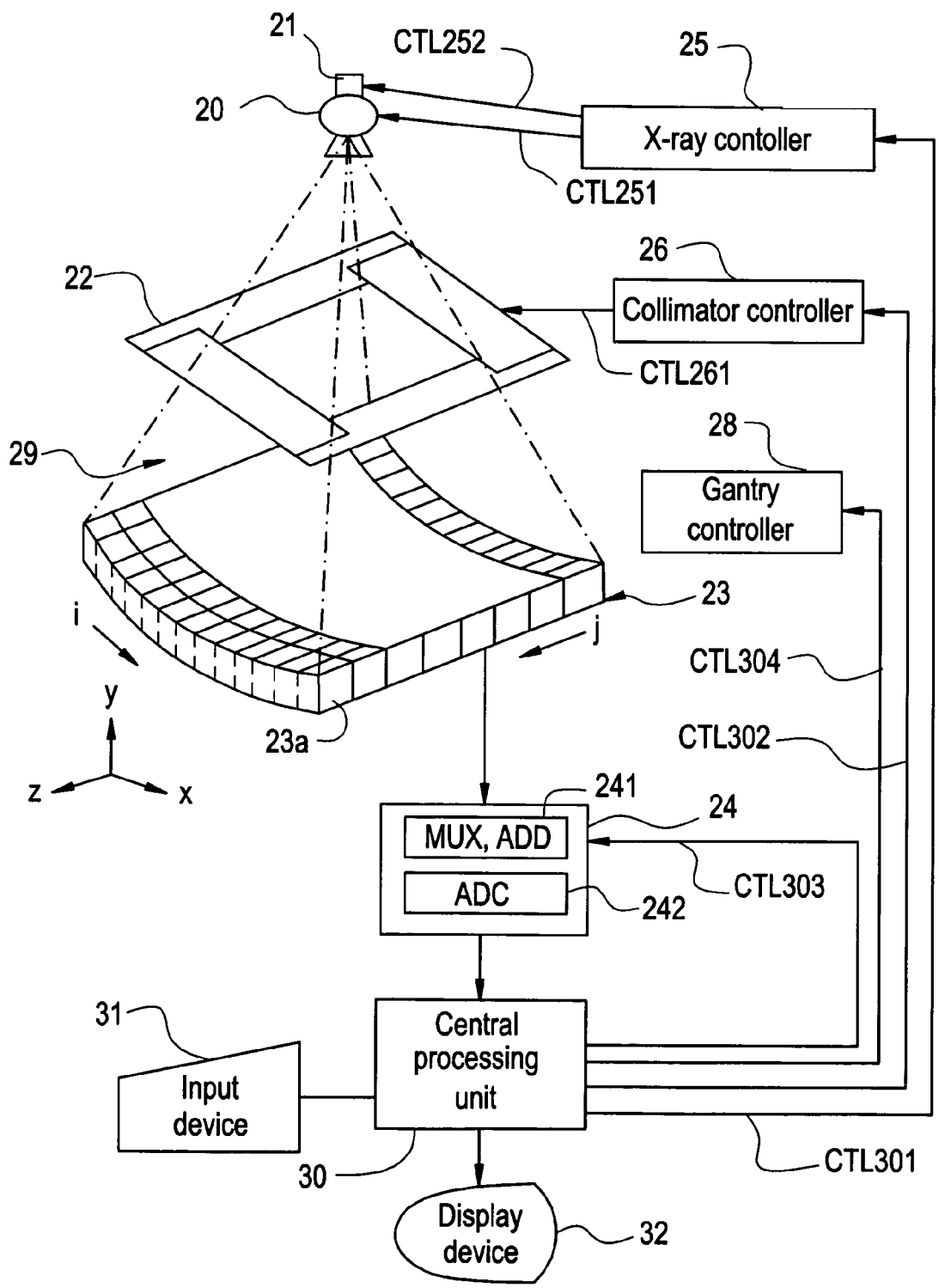
FIG. 2 shows the configuration of a major portion of the X-ray CT system in accordance with the first embodiment of the present invention.

FIG. 1 is a block diagram showing the overall configuration of an X-ray CT system 1 in accordance with the first embodiment of the present invention. FIG. 2 shows the configuration of the major portion of the X-ray CT system 1 in accordance with the first embodiment of the present invention.

As shown in FIG. 1, the X-ray CT system 1 includes a scanner gantry 2, an operator console 3, a first transporter 4, and a second transporter 5.

The scanner gantry 2 will be described below.

Figure 3:
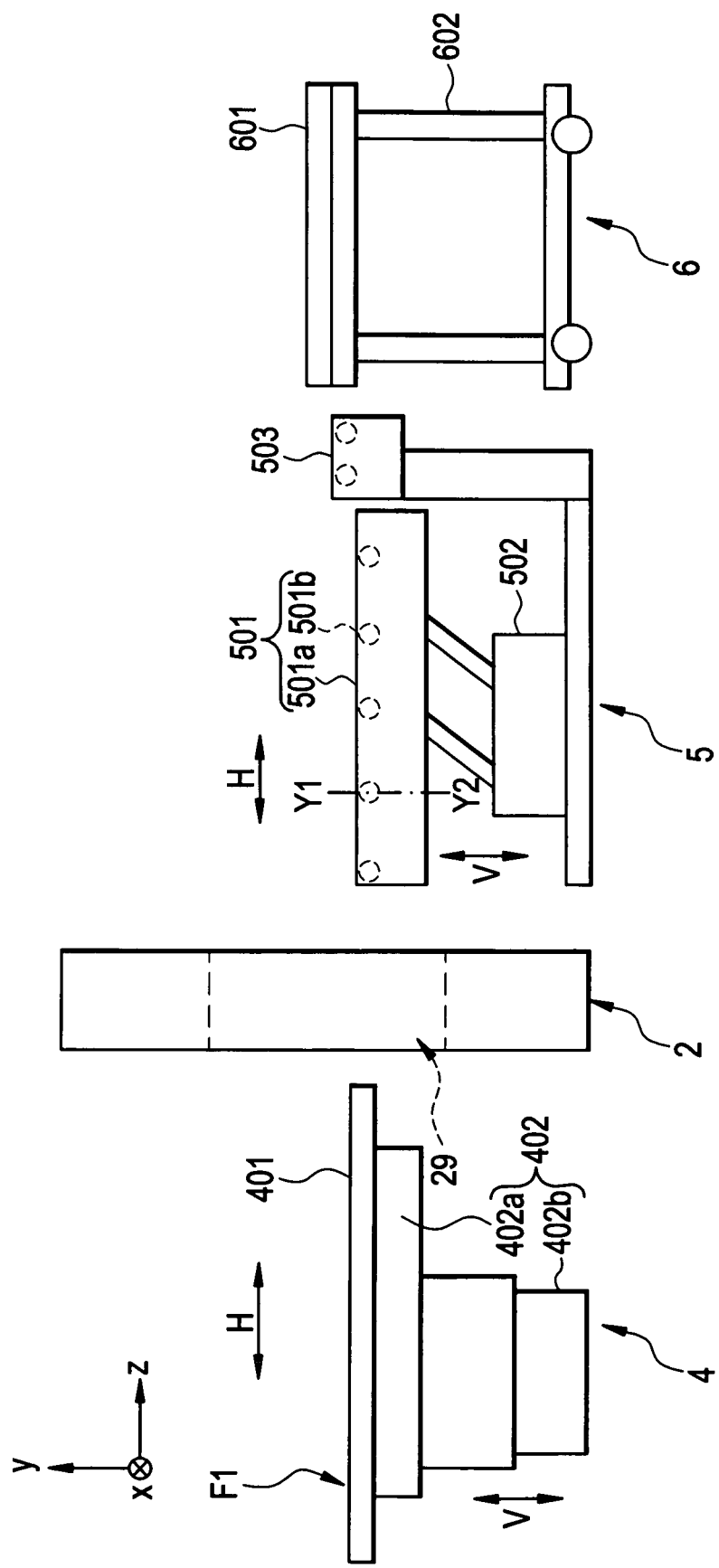
FIG. 3 includes side views showing a scanner 2, a first transporter 4, and a second transporter 5 included in the first embodiment of the present invention.

The scanner gantry 2 scans a subject, who has been transported to a radiographic space 29, with X-rays according to a control signal CTL30a sent from the operator console 3, and obtains projection data items of the subject as raw data. The scanner gantry 2 includes, as shown in FIG. 1, an X-ray tube 20, an X-ray tube mover 21, a collimator 22, an X-ray detector 23, a data acquisition unit 24, an X-ray controller 25, a collimator controller 26, a rotator 27, and a gantry controller 28. In the scanner gantry 2, the X-ray tube 20 and X-ray detector 23 are, as shown in FIG. 3, disposed to sandwich the radiographic space 29 into which the subject is transported. The collimator 22 is disposed to reshape X-rays irradiated from the X-ray tube 20 to the subject lying down in the radiographic space 29. The scanner gantry 2 rotates the X-ray tube 20, collimator 22, and X-ray detector 23 about the subject with the direction z of the subject's body axis as a center. At this time, the X-ray tube 20 irradiates X-rays, and the X-ray detector 23 detects X-rays which transmit the subject so as to produce projection data items. According to the present embodiment, the scanner gantry 2 scans the subject, who lies down on a transfer board moved from a stretcher, in the radiographic space, and obtains the projection data items of the subject as raw data. The components of the scanner gantry 2 will be described sequentially.

The X-ray tube 20 is of, for example, a rotating anode type and irradiates X-rays to a subject. The X-ray tube 20 irradiates, as shown in FIG. 2, X-rays of a predetermined intensity according to a control signal CTL251 sent from the X-ray controller 25. The X-rays irradiated from the X-ray tube 20 are, for example, conically reshaped by the collimator 22, and irradiated to the subject lying down in the radiographic space 29. Thereafter, the X-rays which transmit the subject are detected by the X-ray detector 23. Herein, the X-ray tube 20 is rotated about the subject with the direction z of the subject's body axis as a center by means of the rotator 27 so that X-rays will be irradiated to the subject in directions of view angles around the subject. In short, the X-ray tube 20 is rotated about the subject with an axis, which extends in a horizontal direction in which the first transporter 4 moves to transport the subject to the radiographic space 29, as a center of rotation.

The X-ray tube mover 21 moves, as shown in FIG. 2, the center of irradiation in the X-ray tube 20 in the direction z of the body axis of the subject lying down in the radiographic space 29 within the scanner gantry 2 according to a control signal CTL252 sent from the X-ray controller 25.

The collimator 22 is, as shown in FIG. 2, interposed between the X-ray tube 20 and X-ray detector 23. The collimator 22 has, for example, two shielding plates, which do not transmit X-rays, disposed in each of a direction i of channels and a direction j of arrays. The collimator 22 moves the two shielding plates, which are disposed in each of the directions, independently of the other two shielding plates according to a control signal CTL 261 sent from the collimator controller 26. Thus, the collimator 22 shields X-rays, which are irradiated from the X-ray tube 20, in each of the directions so as to reshape the X-rays conically, and adjusts the range of X-irradiation. In other words, the collimator 22 varies the size of an opening, through which X-rays irradiated from the X-ray tube 20 pass, so as to adjust the range of X-irradiation.

The X-ray detector 23 detects X-rays that are irradiated from the X-ray tube 20 and transmit a subject so as to produce projection data items of the subject. The X-ray detector 23 is rotated together with the X-ray tube 20 about the subject by means of the rotator 27. The X-ray detector 23 detects the X-rays, which are irradiated from the X-ray tube 20 around the subject and transmit the subject, so as to produce projection data items.

As shown in FIG. 2, the X-ray detector 23 includes a plurality of detector elements 23a. The X-ray detector 23 has the detector elements 23a arrayed two-dimensionally in the direction i of channels corresponding to a direction of rotation in which the X-ray tube 20 is rotated by the rotator 27 with the subject, who lies down in the radiographic space 29, as a center, and in the direction j of arrays corresponding to the direction of an axis of rotation serving as a center axis about which the X-ray tube 20 is rotated by the rotator 27. For example, the X-ray detector 23 has about 1000 detector elements 23a arrayed in the direction i of channels and about 32 to 64 detector elements 23 arrayed in the direction j of arrays. Moreover, the X-ray detector 23 has a cylindrically concave surface formed by the plurality of two-dimensionally arrayed detector elements 23a.

The detector elements 23a constituting the X-ray detector 23 are, for example, solid-state detectors, and each include a scintillator (not shown) that converts X-rays into light and a photodiode (not shown) that converts the light produced by the scintillator into charge. The detector elements 23a may be realized with semiconductor detector elements utilizing cadmium telluride (CdTe) or ion chamber-type detector elements utilizing xenon gas (Xe).

The data acquisition unit 24 is intended to acquire projection data items produced by the X-ray detector 23. The data acquisition unit 24 acquires projection data which each of the detector elements 23a constituting the X-ray detector 23 produces by detecting X-rays, and transfers the projection data to the operator console 3. As shown in FIG. 2, the data acquisition unit 24 includes a selection/addition switching circuit (MUX,ADD) 241 and an analog-to-digital converter (ADC) 242. The selection/addition switching circuit 241 selects any of projection data items produced by the respective detector elements 23a included in the X-ray detector 23 according to a control signal CTL303 sent from a central processing unit 30 or varies and summates a set of projection data items and transfers the result of the summation to the analog-to-digital converter 242. The analog-to-digital converter 242 converts the selected projection data or the projection data resulting from the summation from an analog form to a digital form, and transfers the digital data to the central processing unit 30.

The X-ray controller 25 transmits, as shown in FIG. 2, a control signal CTL251 to the X-ray tube 20 according to a control signal CTL301 sent from the central processing unit 30, and thus controls X-irradiation. The X-ray controller 25 controls, for example, the tube current of the X-ray tube 20 or the irradiation time thereof. Moreover, the X-ray controller 25 transmits a control signal CTL 252 to the X-ray tube mover 221 according to a control signal CTL301 sent from the central processing unit 30, and thus controls the X-ray tube 20 so that the center of irradiation in the X-ray tube 20 will be moved in the body-axis direction z.

The collimator controller 26 transmits, as shown in FIG. 2, a control signal CTL261 to the collimator 22 according to a control signal CTL302 sent from the central processing unit 30, and thus controls the collimator 22 so that the collimator 22 will reshape X-rays irradiated from the X-ray tube 20 to a subject.

The rotator 27 is, as shown in FIG. 1, shaped like a cylinder and has the radiographic space 29, which accommodates a subject, formed in the center thereof. The rotator 27 drives, for example, a motor (not shown) according to a control signal CTL28 sent from the gantry controller 28 so as to rotate itself about the subject with the direction z of the body axis of the subject lying down in the radiographic space 29 as a center. The rotator 27 includes and bears the X-ray tube 20, X-ray tube mover 21, collimator 22, X-ray detector 23, data acquisition unit 24, X-ray controller 25, and collimator controller 26. The rotator 27 supplies power to the components via a slip ring (not shown). Moreover, the rotator 27 rotates the components about the subject, and varies the positional relationships of the components to the subject, who has been transported into the radiographic space 29, in a direction of rotation.

The gantry controller 28 transmits, as shown in FIG. 1 and FIG. 2, a control signal CTL28 to the rotator 27 according to a control signal CTL304 sent from the central processing unit 30 included in the operator console 3, and thus controls the rotator 27 so that the rotator 27 will rotate itself.

The operator console 3 will be described below.

The operator console 3 includes, as shown in FIG. 1, the central processing unit 30, an input device 31, a display device 32, and a storage device 33. The components will be described sequentially.

The central processing unit 30 included in the operator console 3 performs various pieces of processing in response to a command which an operator enters at the input device 31. The central processing unit 30 includes a computer and programs causing the computer to serve as various pieces of means, and further includes, as shown in FIG. 1, a control unit 301 and an image production unit 302.

The control unit 301 included in the central processing unit 30 controls the components so that X-rays will be irradiated from the X-ray tube 20 to a subject according to the conditions for scanning the subject and the X-rays which transmit the subject will be detected by the X-ray detector 23. Specifically, the control unit 301 transmits a control signal CTL30a to the components according to the scanning conditions so that a scan will be performed. For example, the control unit 301 transmits a control signal CTL30b to the subject transporter 4 so that the subject transporter 4 will transport a subject to the inside or outside of the radiographic space 29. Moreover, the control unit 301 transmits a control signal CTL304 to the gantry controller 28 so as to rotate the rotator 27 included in the scanner gantry 2. Moreover, the control unit 301 transmits a control signal CTL301 to the X-ray controller 25 so that X-rays will be irradiated from the X-ray tube 20. The control unit 301 transmits a control signal CTL302 to the collimator controller 26 so that the collimator 22 will be controlled to reshape X-rays. Moreover, the control unit 42 transmits a control signal CTL303 to the data acquisition unit 24 and thus controls the data acquisition unit 24 so that the data acquisition unit 24 will acquire projection data produced by each of the detector elements 23a included in the X-ray detector 23.

The image production unit 302 included in the central processing unit 30 produces a tomographic image of a subject according to projection data items acquired by the scanner gantry 2. The image production unit 302 performs preprocessing, which includes sensitivity correction and beam hardening compensation, on projection data items produced based on X-rays irradiated in a plurality of directions of view angles during a helical scan, and reconstructs a tomographic image, which expresses a subject's plane, according to a filtering back projection technique.

The input device 31 is realized with, for example, a keyboard and a mouse. The input device 31 transfers various pieces of information including scanning parameters and patient data and various commands to the central processing unit 30 according to an operator's manipulation. For example, when the scanning conditions are designated, the input device 31 transfers as the scanning parameters a start position of scanning, an end position of scanning, a scan pitch, an X-ray beam width, a tube current, and a slice thickness in response to a command entered by the operator.

The display device 32 includes, for example, a CRT, and displays an image on a display surface thereof in response to a command sent from the central processing unit 30. For example, a tomographic image produced by the image production unit 302 is displayed on the display surface of the display device 32.

The storage device 33 included in the operator console 3 is realized with a memory. Various data items are stored in the storage device 33. The data items stored in the storage device 33 are accessed by the central processing unit whenever they are needed.

The first transporter 4 and second transporter 5 will be described below.

Figure 4:
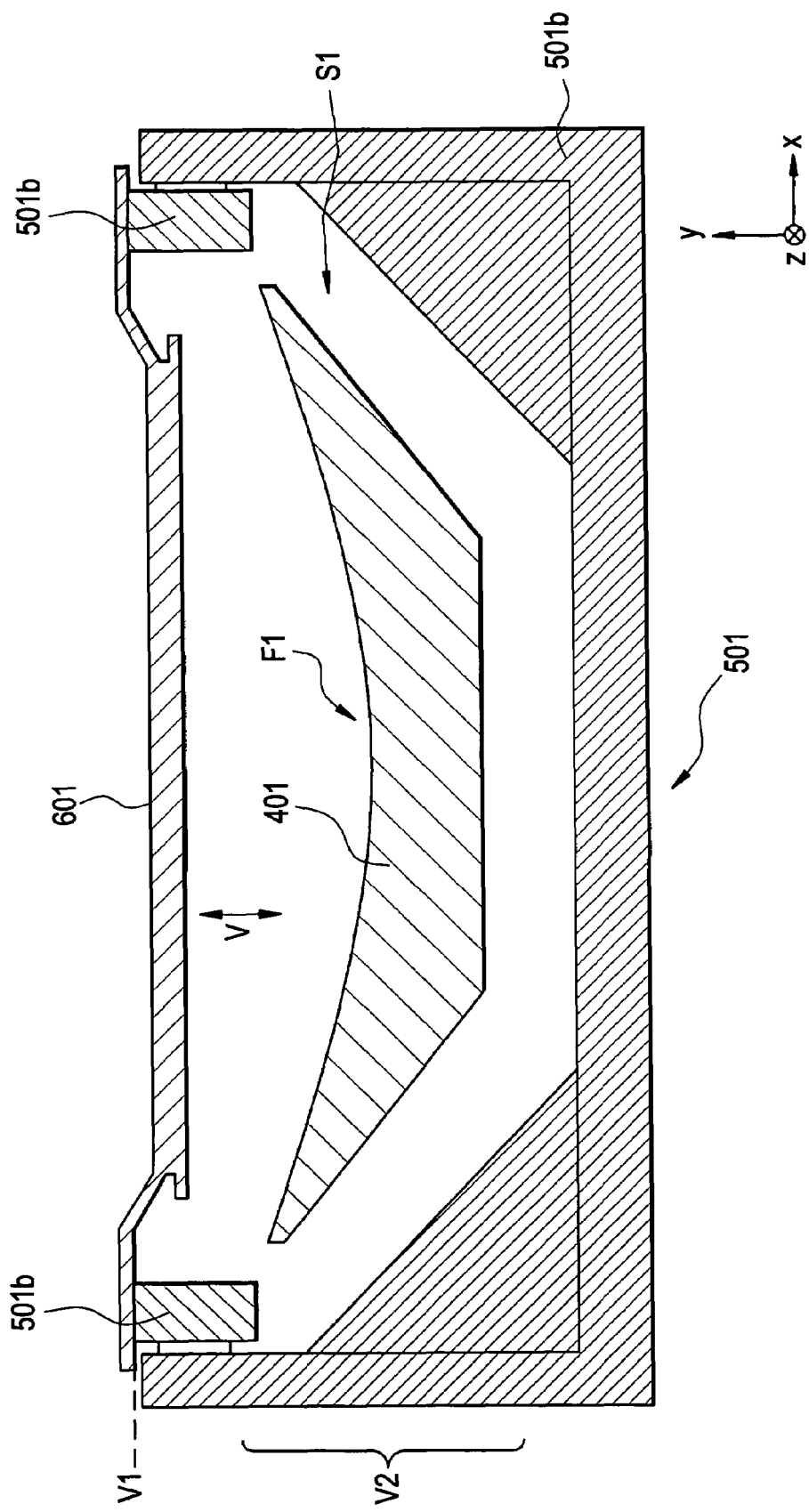
FIG. 4 shows a Y1-Y2 section of the second transporter shown in FIG. 3 and included in the first embodiment of the present invention.

FIG. 3 includes side views showing the scanner 2, first transporter 4, and second transporter 5 included in the X-ray CT system 1 in accordance with the first embodiment of the present invention. FIG. 4 is a sectional view of the second transporter 5 included in the first embodiment of the present invention, and shows a Y1-Y2 section of the second transporter 5 shown in FIG. 3.

The first transporter 4 includes, as shown in FIG. 3, a radiographic table 401 and a radiographic table mover 402. A transfer board 601 on which a subject lies down is moved from a stretcher 6 to the first transporter 4 via the second transporter 5. The first transporter 4 bears the moved transfer board 601 and moves the borne transfer board 601 to the radiographic space 29 in the scanner gantry 2. The components of the first transporter 4 will be described below.

The radiographic table 401 included in the first transporter 5 is, as shown in FIG. 3, a table having a placement surface F1 thereof extended in horizontal directions H, and borne by the radiographic table mover 402. The radiographic table 401 is moved in one of the horizontal directions H by the radiographic table mover 402 so that it will jut out to enter the radiographic space 29. The transfer board 601 on which a subject lies down is, as detailed later, moved from the stretcher 6 to the placement surface F1 of the radiographic table 401 via the second transporter 5 outside the radiographic space 29. The radiographic table 401 bears the transfer board 601 moved onto the placement surface thereof F1. For example, the transfer board 601 on which a subject lies down on his/her back is moved to the radiographic table 401.

The radiographic table mover 402 included in the first transporter 5 includes, as shown in FIG. 3, a radiographic table horizontal mover 402a and a radiographic table vertical mover 402b. The radiographic table mover 402 has the radiographic table horizontal mover 402a and radiographic table vertical mover 402b thereof controlled based on a control signal CTL30b sent from the central processing unit 30, and thus moves the radiographic table 401.

Now, the radiographic table horizontal mover 402a bears, as shown in FIG. 3, the radiographic table 401, and moves the radiographic table 401 in the horizontal directions H. For example, the radiographic table horizontal mover 402a drives a motor (not shown) to move the radiographic table 401 in the direction z of the body axis of the subject lying down on the radiographic table 401. According to the present embodiment, as shown in FIG. 3, an intermediate table 501 is included in the second transporter 5 so that the intermediate table 501 will be opposed to the radiographic table 401 with the radiographic space between them in one of the horizontal directions H in which the radiographic table horizontal mover 402a moves the radiographic table 401. The radiographic table horizontal mover 402a moves the radiographic table 401 in one of the horizontal directions H so that the radiographic table 401 will head for the second transporter 5 via the radiographic space 29. Consequently, the radiographic table 401 is stored in a storage space S1 in the intermediate table 501 shown in FIG. 4. The transfer board 601 borne by the intermediate table 501 and the radiographic table 401 stored in the storage space S1 of the intermediate table 501 are moved to approach each other. After the transfer board 601 is borne by the radiographic table 401, the radiographic table horizontal mover 402a moves the radiographic table 401, which bears the transfer board 601, in the other horizontal direction H to the radiographic space 29.

Moreover, the radiographic table vertical mover 402b bears, as shown in FIG. 3, the radiographic table horizontal mover 402a, and moves the radiographic table 401 in vertical directions V perpendicular to a horizontal plane. For example, the radiographic table vertical mover 402b drives a hydraulic actuator (not shown) so as to move the radiographic table 401 in the vertical directions V.

On the other hand, the second transporter 5 includes, as shown in FIG. 3, the intermediate table 501, an intermediate table mover 502, and a stretcher coupler 503. The transfer board 601 on which a subject lies down is moved from the stretcher 6 to the second transporter 5. The second transporter 5 bears the moved transfer board 601, and moves the borne transfer board 601 to the radiographic table 401 included in the first transporter 4. The components of the second transporter 5 will be described below.

The radiographic table 401 is, as shown in FIG. 3, opposed to the intermediate table 501 included in the second transporter 5 with the radiographic space 29 of the scanner gantry 2 between them the radiographic table horizontal mover 402a in the body-axis direction z corresponding to one of the horizontal directions H in which the radiographic table horizontal mover 402a moves the radiographic table 401. Moreover, the intermediate table 501 includes, as shown in FIG. 3, an intermediate table body 501a and rollers 501b. As shown in FIG. 4, the intermediate table 501 bears the transfer board 601 that is moved from the stretcher 6, and has the radiographic table 401 stored in the storage space S1 thereof. The transfer board 601 is moved from the stretcher 6 to the intermediate table 501 in a direction opposite to the body-axis direction z corresponding to one of the horizontal directions H in which the radiographic table horizontal mover 402a moves the radiographic table 401.

Now, the intermediate table body 501a is, as shown in FIG. 3, a table extending in the horizontal directions H and borne by the intermediate table mover 502. The intermediate table body 501a has, as shown in FIG. 4, the storage space S1 formed therein, and has the rollers 501b disposed inside. More specifically, the intermediate table body 501a has the rollers 501b disposed on the internal wall thereof facing the storage space S1 so that the rollers 501b can bear the transfer board, which is moved from the stretcher 6, at a first position V1 in one of the vertical directions V. Moreover, the intermediate table body 501a has the storage space S1 formed at a second position V2 lower in the vertical direction V than the first position V1 at which the transfer board 601 is borne. The radiographic table 401 is stored in the storage space S1 while being separated from the transfer board 601 borne at the first position V1.

Moreover, the rollers 501b are disposed near the opening of the storage space S1 formed in the intermediate table body 501a so that they will bear the transfer board 601, which is moved from the stretcher 6, above the second position V2 in the vertical direction V at which the radiographic table 401 is stored in the storage space S1. The rollers 501b are disposed on the internal wall of the intermediate table body facing the storage space S1 so that they will meet both the ends of the transfer board 601 which is moved from the stretcher 6 in the direction opposite to the body-axis direction z. The rollers 501b bear the transfer board 601 so that the transfer board 601 can be moved in the direction opposite to the body-axis direction z. The plurality of rollers 501b are, as shown in FIG. 3, disposed in the body-axis direction z which corresponds to one of the horizontal directions H and in which the radiographic table horizontal mover 402b moves the radiographic table 401 to the storage space S1 in the intermediate table body 501a.

The intermediate table mover 502 included in the second transporter 5 bears, as shown in FIG. 3, the intermediate table 501 and moves the intermediate table 501 in the vertical directions V and horizontal directions H alike. The intermediate table mover 502 has two parallel links formed with link members whose ends are fixed to a rotation shaft and which are parallel to each other. The parallel links bear the intermediate table 501. The intermediate table mover 502 varies an angle, at which a direction in which the parallel links extend and one of the horizontal directions H meet, by moving the parallel links with the rotation shaft as a center using a hydraulic actuator (not shown). Thus, the intermediate table mover 502 moves the intermediate table 501 in the vertical directions V and horizontal directions H alike. For example, a footswitch (not shown) is used to drive the hydraulic actuator. The intermediate table mover 502 thus moves the intermediate table 501 in the vertical directions V and horizontal directions H, whereby the transfer board 601 borne by the intermediate table 502 and the radiographic table 401 stored in the storage space S of the intermediate table 502 approach each other. The transfer board 601 is moved to and borne by the radiographic table 501. In other words, the intermediate table mover 502 moves the intermediate table 501 in a vertical direction V from the first position V1 to the second position V2, whereby the transfer board borne by the intermediate table 501 at the first position V1 is moved to and borne by the radiographic table 601 stored in the storage space S1.

The stretcher coupler 503 is coupled and fixed to the stretcher 6. In the present embodiment, the stretcher coupler 503 is coupled and fixed to a cart 602 of the stretcher 6. For example, the stretcher coupler 503 is coupled and fixed to the cart 602 using a chain and a hook with which the chain is locked. Moreover, the stretcher coupler 503 has a supporting surface that supports the transfer board 601 moved from the stretcher 6 and that is flush with the surface of the stretcher 6 on which the transfer board 601 is placed.

Actions to be performed in the X-ray CT system 1 in accordance with the present embodiment will be described below.

Figure 5:
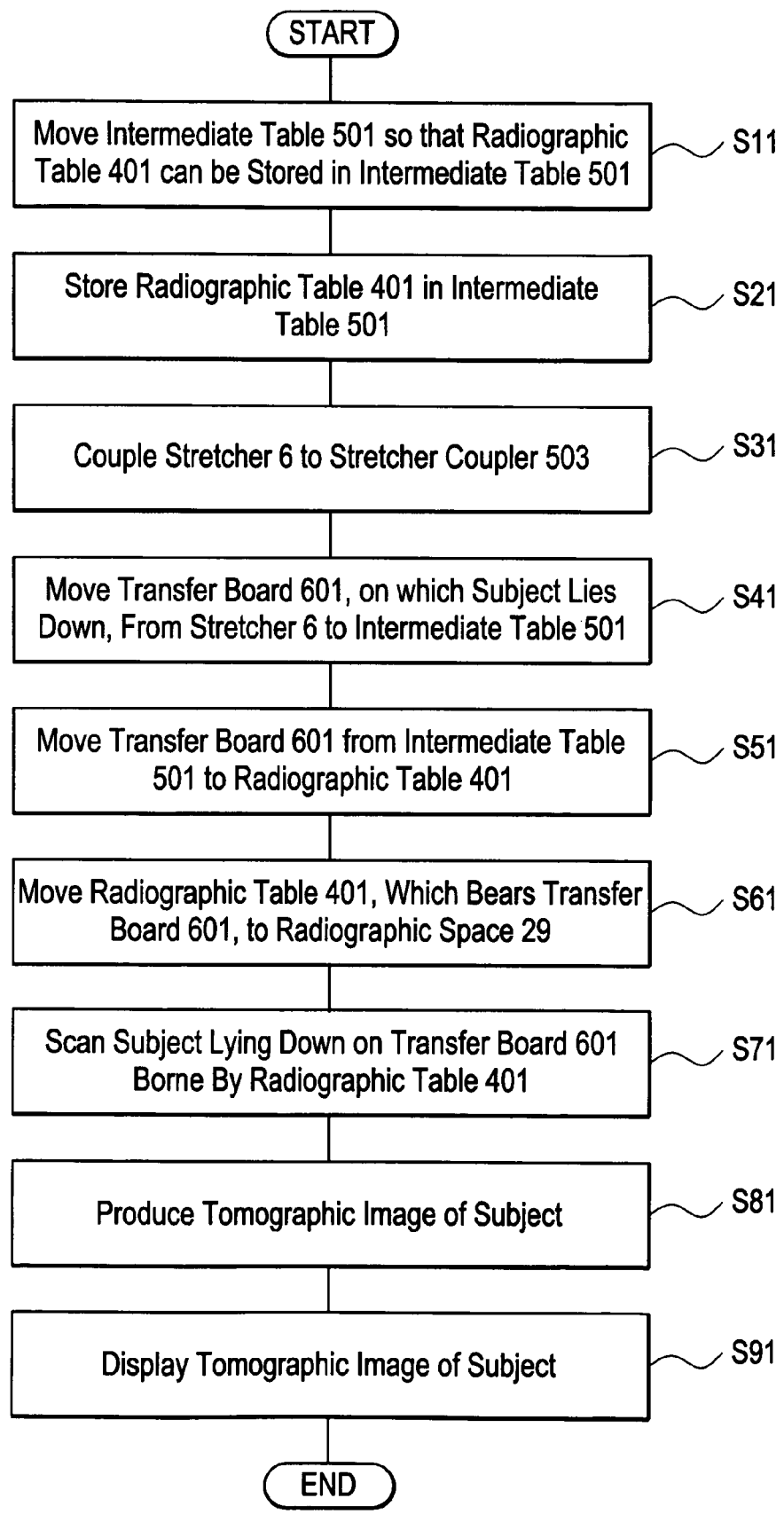
FIG. 5 is a flowchart describing actions to be performed in order to scan a subject using the X-ray CT system in accordance with the first embodiment of the present invention.

FIG. 5 is a flowchart describing actions to be performed for scanning a subject using the X-ray CT system 1 in accordance with the first embodiment of the present invention.

To begin with, as described in FIG. 5, the intermediate table 501 is moved so that the radiographic table 401 can be stored in the intermediate table 501 (S11).

Herein, the intermediate table mover 502 moves the intermediate table 501.

Figure 6:
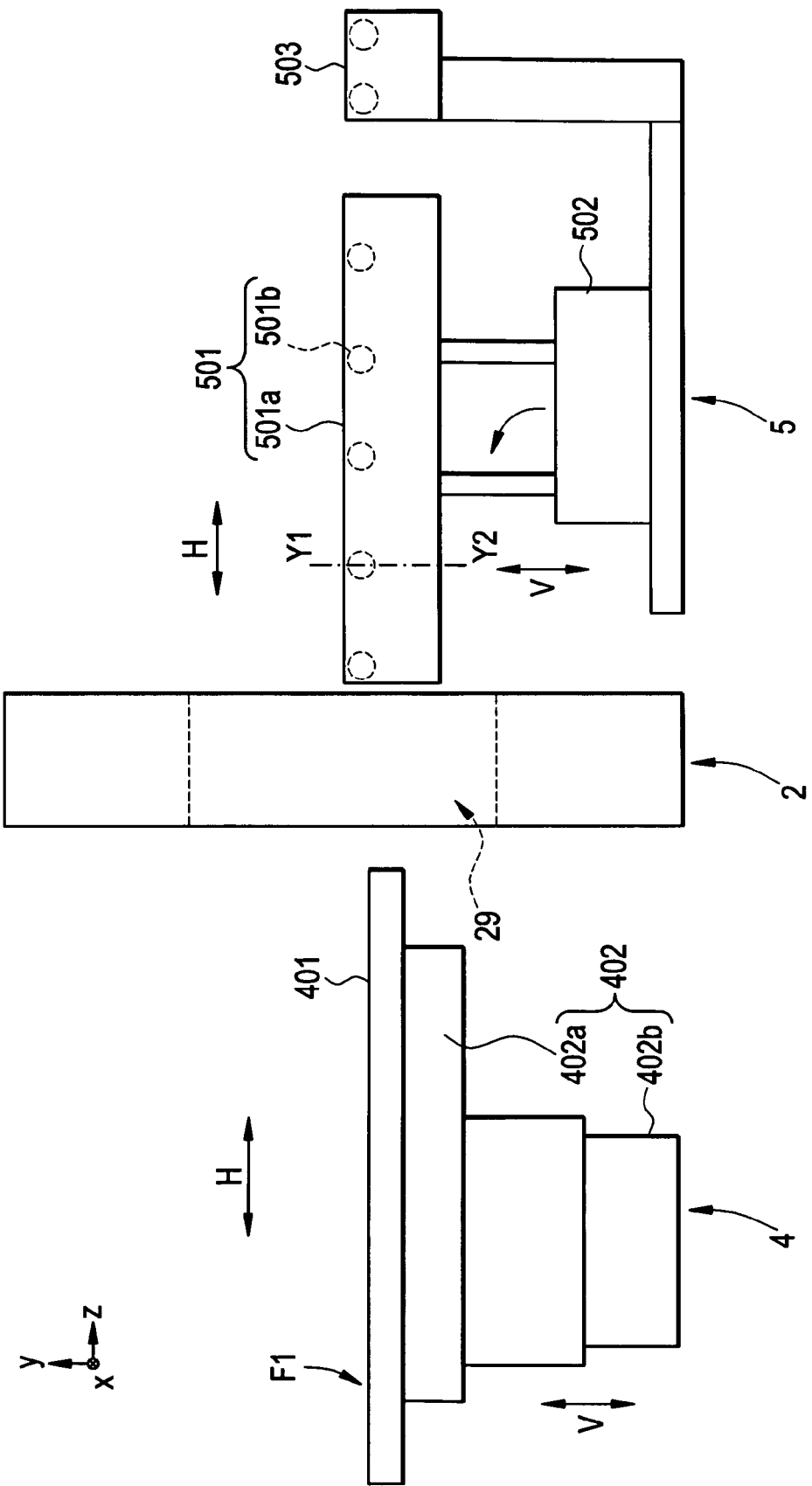
FIG. 6 includes side views showing the movement of an intermediate table 501 made by an intermediate table mover 502 so that a radiographic table 401 can be stored in the intermediate table 501 according to the first embodiment of the present invention.

FIG. 6 includes side views showing the movement of the intermediate table 501 made by the intermediate table mover 502 so that the radiographic table 401 can be stored in the intermediate table 501 included in the first embodiment of the present invention.

As shown in FIG. 6, the intermediate table mover 502 moves the parallel links with the rotation shaft as a center so as to vary the angle at which the direction in which the parallel links extend and one of the horizontal directions H meet. Consequently, the intermediate table 501 is moved in the vertical directions V and horizontal directions H. The heights of the radiographic table 501 and intermediate table 501 in a vertical direction V are adjusted so that the radiographic table 501 can be stored in the intermediate table 501.

Next, as described in FIG. 5, the radiographic table 401 is stored in the intermediate table 501 (S21).

Herein, the radiographic table horizontal mover 402a moves the radiographic table 401 so that the radiographic table 401 will be stored in the intermediate table 501.

Figure 7:
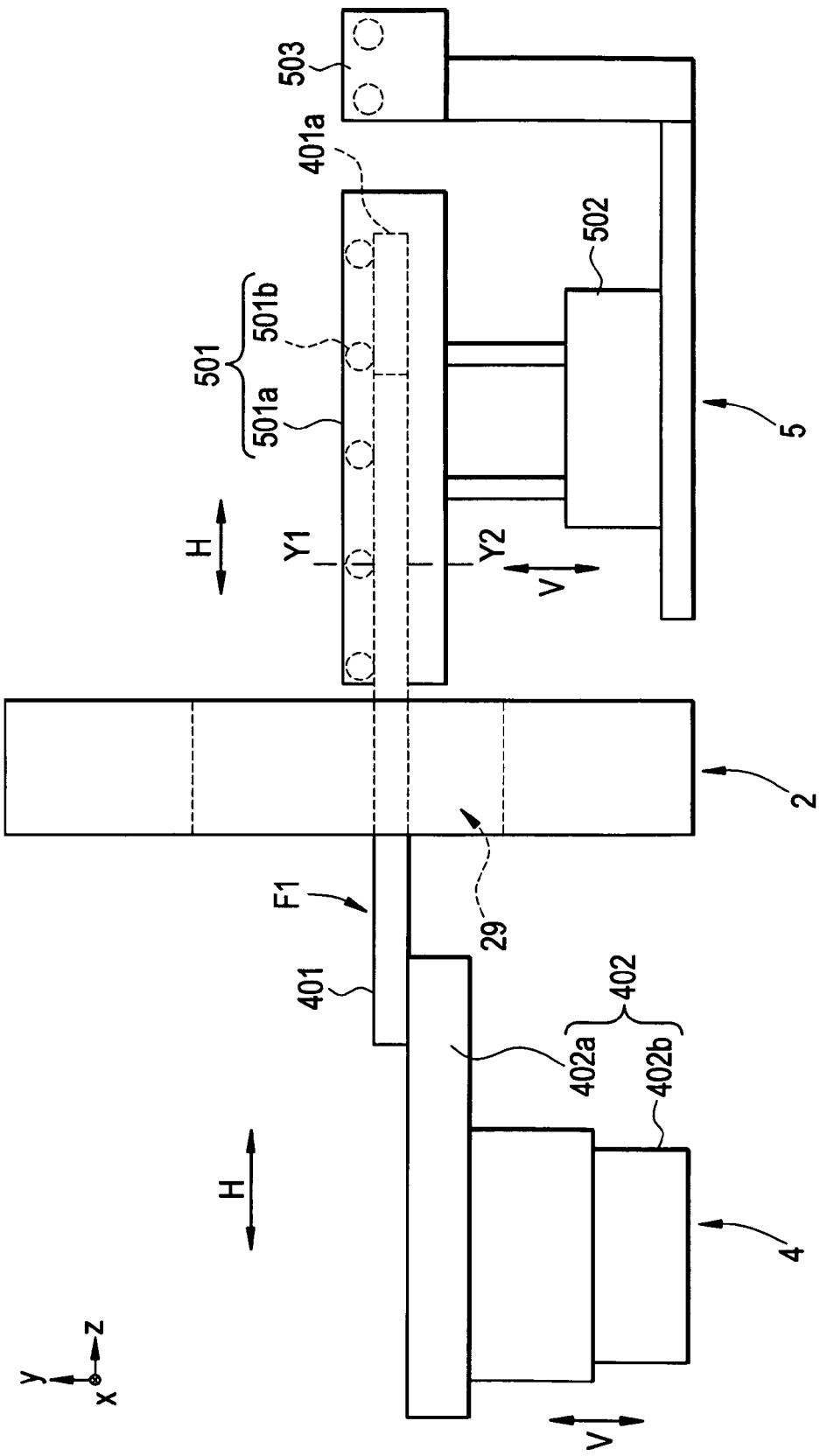
FIG. 7 includes side views showing the storage of the radiographic table 401 moved by a radiographic table horizontal mover 402a in the intermediate table 501 according to the first embodiment of the present invention.

FIG. 7 includes side views showing the movement and storage of the radiographic table 401 made by the radiographic table horizontal mover 402a included in the first embodiment of the present invention so that the radiographic table.

As shown in FIG. 7, the radiographic table horizontal mover 402a moves the radiographic table 401 in a horizontal direction H so that the radiographic table 401 will head for the second transporter 5 via the radiographic space 29. Herein, an extender 401a with which the placement surface F1 is extended is fixed to the end of the radiographic table 401, and the radiographic table 401 is moved in the horizontal direction H. Consequently, as shown in FIG. 4, the radiographic table 401 is stored in the storage space S1 of the intermediate table 501. Herein, the radiographic table 401 is stored in the storage space S1 below the first position V1 in the intermediate table 501 so that the radiographic table 401 will be separated from the transfer board 601 borne at the first position V1.

Thereafter, as described in FIG. 5, the stretcher 6 is coupled to the stretcher coupler 503 (S31).

An operator transports the stretcher 6, which has a subject loaded on the transfer board 601 thereof, from outside, and couples and fixes the stretcher 6 to the stretcher coupler 503.

Thereafter, as described in FIG. 5, the transfer board 601 on which the subject lies down is moved from the stretcher 6 to the intermediate table 501 (S41).

Herein, the operator dismounts the transfer board 601, on which the subject lies down, from the cart 602 of the stretcher 6, and moves the transfer board 601 to the intermediate table 501.

Figure 8:
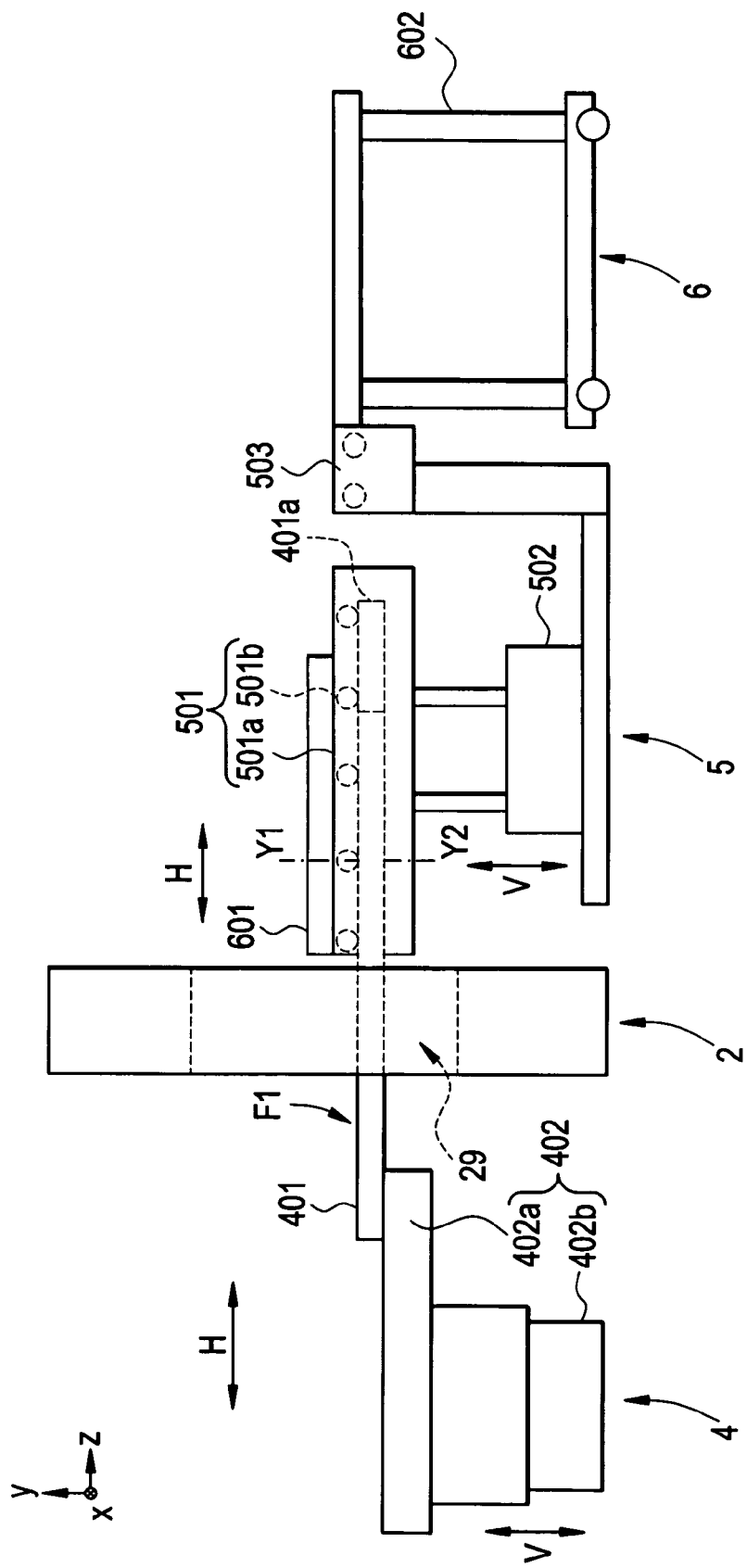
FIG. 8 includes side views showing the movement of a transfer board 601 from a stretcher 6 to the intermediate table 501 according to the first embodiment of the present invention.

FIG. 8 includes side views showing the movement of the transfer board 601 from the stretcher 6 to the intermediate table 501 included in the first embodiment of the present invention.

As shown in FIG. 8, the transfer board 601 on which the subject lies down is slid from the stretcher 6 to the intermediate table 501 via the stretcher coupler 503. Specifically, the operator slides the transfer board 601 over the plurality of rollers 501b in a horizontal direction H in which the plurality of rollers 501b are disposed in the intermediate table 501. Herein, as shown in FIG. 4, the transfer board 601 is slid so that the transfer board 601 will be opposed to the placement surface F1 of the radiographic table 401 stored in the storage space S1 of the intermediate table 501. The transfer board 601 is borne by the rollers 501b included in the intermediate table 501.

Thereafter, as described in FIG. 5, the transfer board 601 is moved from the intermediate table 501 to the radiographic table 401 (S51).

Herein, the intermediate table mover 502 moves the intermediate table 501, whereby the transfer board is moved to and borne by the radiographic table 601.

Figure 9:
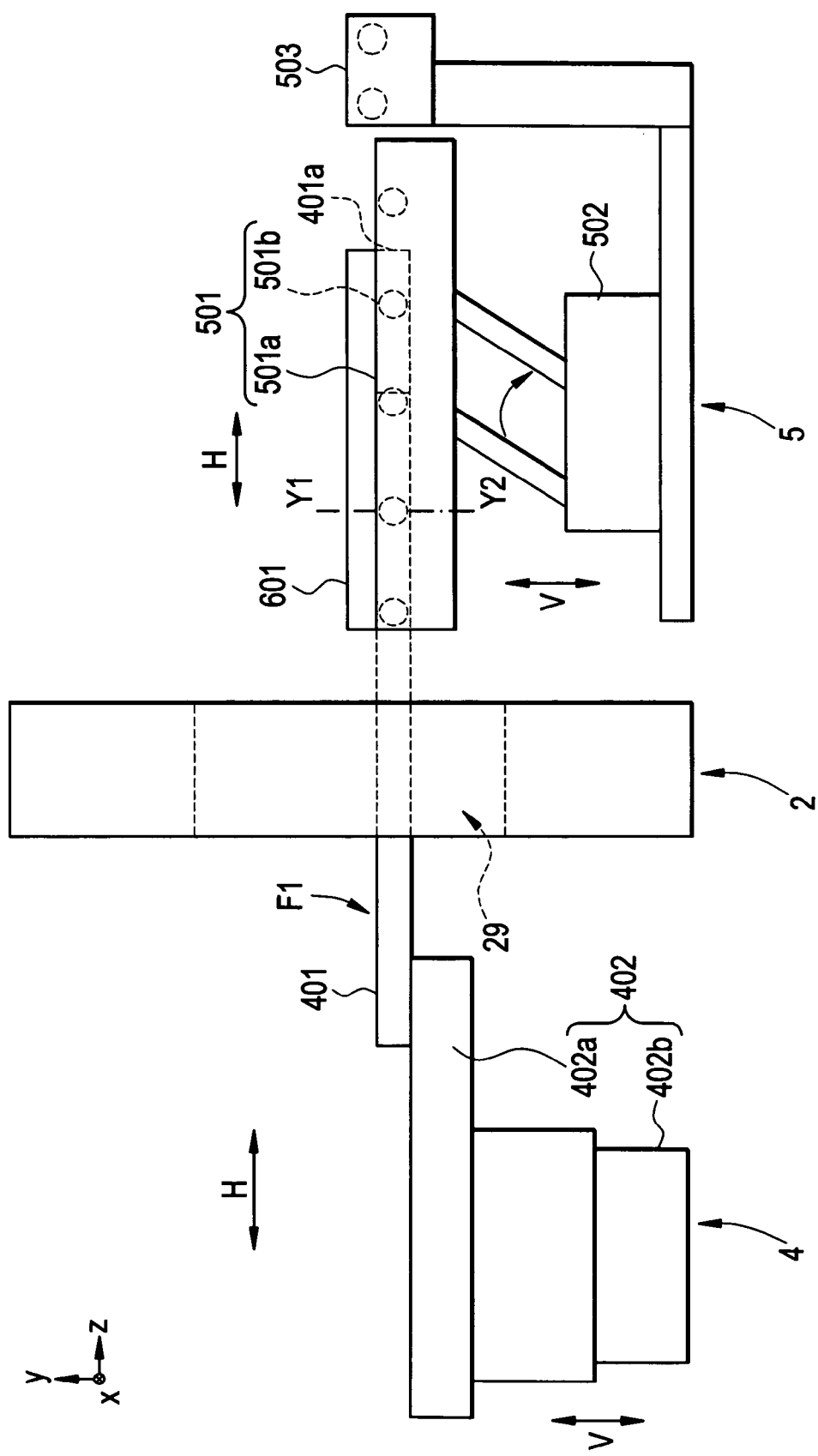
FIG. 9 includes side views showing the movement of the transfer board 601 from the intermediate table 501 to the radiographic table 401 according to the first embodiment of the present invention.

FIG. 9 includes side views showing the movement of the transfer board 601 from the intermediate table 501 to the radiographic table 401 included in the first embodiment of the present invention.

As shown in FIG. 9, the intermediate table mover 502 moves the intermediate table 501 downwards in a vertical direction V, whereby the transfer board 601 borne by the intermediate table 501 and the radiographic table 401 stored in the storage space S of the intermediate table 502 approach each other. Consequently, the transfer board 601 is moved to and borne by the radiographic table 401.

Specifically, as shown in FIG. 4, the intermediate table mover 502 moves the intermediate table 501 from the first position V1 to the second position V2 in the vertical direction V. Thus, the transfer board borne by the intermediate table 501 at the first position V1 is moved to the radiographic table 601 that is stored in the storage space S1 at the second position V2 and borne by the radiographic table vertical mover 402b. The transfer board 601 borne by the rollers 501b included in the intermediate table 501 is brought into contact with the placement surface F1 of the radiographic table 401, and then borne by the radiographic table 401.

Thereafter, as described in FIG. 5, the radiographic table 401 bearing the transfer board 601 is moved to the radiographic space 29 (S61).

Herein, the radiographic table 401 bearing the transfer board 601 is moved towards the radiographic space 29 in a horizontal direction H by means of the radiographic table horizontal mover 402a.

Thereafter, as described in FIG. 5, the subject lying down on the transfer board 601 borne by the radiographic table 401 is scanned (S71).

Herein, the scanner gantry 2 scans the subject, who has been moved to the radiographic space 29, using X-rays so as to obtain projection data items of the subject as raw data. For example, the scanner gantry 2 scans the subject according to a helical scanning technique so as to obtain the projection data items.

Thereafter, as described in FIG. 5, a tomographic image of the subject is produced (S81).

Based on the projection data items obtained by the scanner gantry 2, the image production unit 302 produces a tomographic image expressing the subject's plane. Specifically, the image production unit 302 performs preprocessing including sensitivity correction and beam hardening compensation on the obtained projection data items, and then reconstructs the tomographic image, which expresses the subject's plane, according to a filtering back projection technique.

Thereafter, as described in FIG. 5, the tomographic image of the subject is displayed (S91).

Herein, the tomographic image produced by the image production unit 302 is displayed on the display surface of the display device 32.

As mentioned above, according to the present embodiment, the intermediate table 501 bears the transfer board 601 moved from the stretcher 6, and the intermediate table mover 502 moves the transfer board 601, which is borne by the intermediate table 501, to the radiographic table 401 so that the intermediate table 501 will be borne by the radiographic table 401. Herein, the transfer board 601 moved from the stretcher 6 is borne by the intermediate table 501 at the first position V1 in a vertical direction V. The radiographic table 401 is stored in the storage space S1 of the intermediate table 501 that is formed at the second position V2 lower in the vertical direction V than the first position V1, so that the radiographic table 401 will be separated downward from the transfer board 601 borne at the first position V1. The intermediate table mover 502 moves the transfer board 601, which is borne by the intermediate table 501, to the radiographic table 401 so that the transfer board 601 will be borne by the radiographic table 401. Herein, the intermediate table mover 502 moves the intermediate table 501 from the first position V1 to the second position V2 in the vertical direction V so that the transfer board 601 borne by the intermediate table 501 at the first position V1 and the radiographic table 501 stored in the storage space S1 of the intermediate table 501 at the second position V2 will approach each other. Consequently, the transfer board 601 is borne by the radiographic table 401. According to the present embodiment, the transfer board 601 is readily moved from the stretcher 6 to the radiographic table 401, and radiography can be efficiently achieved. Moreover, the present embodiment can prevent application of impacts such as vibrations to the subject during the movement. Moreover, the present embodiment contributes to realization of a simple configuration and reduction in a cost because an adverse effect of a warp of the radiographic table 401 is limited.

According to the present embodiment, the intermediate table 501 is installed so that it will be opposed to the radiographic table 401 with the radiographic space 29 between them in one of the horizontal directions H in which the radiographic table horizontal mover 402b moves the radiographic table 401. The radiographic table horizontal mover 402b moves the radiographic table 401 in the horizontal direction H by way of the radiographic space 29, and thus stores the radiographic table 401 in the storage space S1 of the intermediate table 501. Thus, according to the present embodiment, a simple configuration is realized based on a general-purpose system. The ready movement of the transfer board 601 from the stretcher 6 to the radiographic table 401 can be achieved at a low cost.

Moreover, according to the present embodiment, the rollers 501b that bear the transfer board 601 moved from the stretcher 6 so that the transfer board can be moved in a horizontal direction H are included in the intermediate table 501. Herein, the plurality of rollers 501b are disposed in a direction in which the radiographic table 401 is moved to the storage space S1 of the intermediate table 501 by the radiographic table horizontal mover 402b. Consequently, according to the present embodiment, the transfer board 601 can be readily moved from the stretcher 6 to the radiographic table 401. Eventually, radiography can be efficiently achieved.

Moreover, according to the present embodiment, the stretcher coupler 503 is coupled to the stretcher 6 that bears the transfer board 601. Consequently, according to the present embodiment, the transfer board 601 can be readily moved from the stretcher 6 to the radiographic table 601. Eventually, radiography can be efficiently achieved.

Second Embodiment

The second embodiment of the present invention will be described below.

Figure 10:
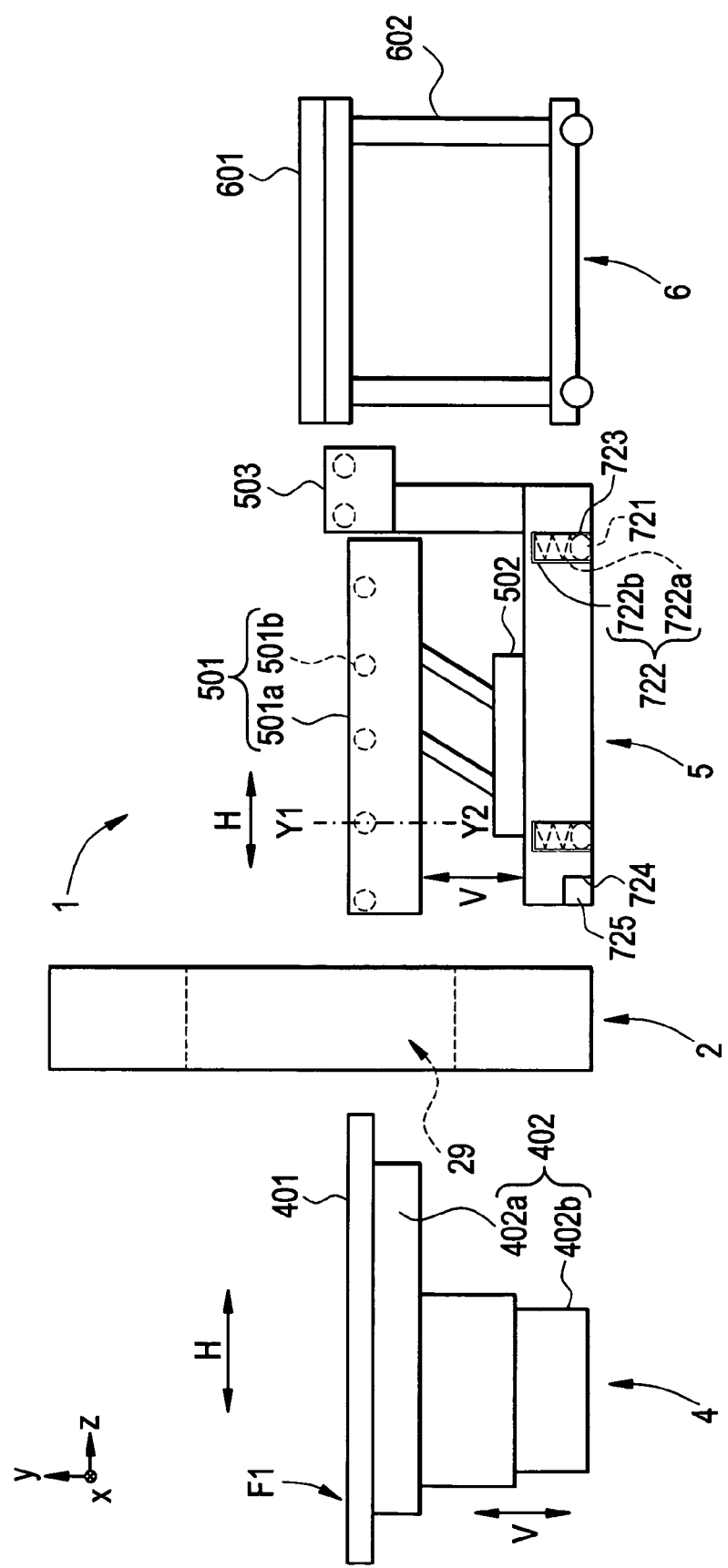
FIG. 10 includes side views showing an X-ray CT system in accordance with the second embodiment of the present invention.

FIG. 10 includes side views showing an X-ray CT system in accordance with the second embodiment of the present invention.

According to the present embodiment, the components of an X-ray CT system are different from those of the X-ray CT system in accordance with the first embodiment. As shown in FIG. 10, the present embodiment further includes caster members 721, a transporter moving mechanism 722, caster receptacles 723, and a body coupler 724. Except this point, the present embodiment is identical to the first embodiment. An iterative description will be omitted.

The caster members 721 each include, as shown in FIG. 10, a wheel that is a rotating body. The wheel is located at one end in a horizontal direction of each of the flanks of the second transporter 5 and at the other end thereof. Herein, the wheels are disposed not only on the flank shown in FIG. 10 but also on the opposite flank. Namely, four wheels are included in total. According to the present embodiment, the second transporter 5 is moved vertically to the wheels of the caster members 721 by means of the transporter moving mechanism 722.

When the second transporter 5 is moved to approach the wheels by the transporter moving mechanism 722, the wheels of the caster members 721 are, as detailed later, put in the respective receiving spaces of the caster receptacles 723. When the second transporter 5 are moved to recede from the wheels by the transporter moving mechanism 722, the wheels of the caster members 721 are moved outside the respective receiving spaces of the caster receptacles 723. Consequently, the second transporter 5 is separated from the floor and borne by the caster members 721.

The transporter moving mechanism 722 is, as shown in FIG. 10, included in the second transporter 5, and moves the second transporter 5 vertically to the caster members 721. Namely, the transporter moving mechanism 722 lifts or lowers the second transporter 5. The transporter moving mechanism 722 causes the second transporter 5 and caster members 721 to approach each other, whereby the caster members 721 are moved into the respective receiving spaces of the caster receptacles 723. Moreover, the transporter moving mechanism 722 causes the second transporter 5 and caster members 721 to recede from each other, whereby the caster members 721 are moved outside the respective receiving spaces of the caster receptacles 723.

According to the present embodiment, the transporter moving mechanism 722 includes springs 722*a* that are disposed at one ends of the wheels of the caster members 721 and that constrain the second transporter 5 to move vertically to the wheels of the caster members 721. The transporter moving mechanism 722 further includes spring supports 722*b* that support the other ends of the springs 722*a*. The springs 722*a* included in the transporter moving mechanism 722 are vertically stretched or contracted in order to move the second transporter 5 vertically to the caster members 721.

For example, when a maintenance worker imposes a load on the second transporter 5 so as to move the second transporter 5 vertically downwards, the springs 722*a* included in the transporter moving mechanism 722 are vertically contracted to cause the second transporter 5 and the caster members 721 to approach each other. Consequently, the transporter moving mechanism 722 introduces the caster members 721 to the receiving spaces of the caster receptacles 723. When the maintenance worker places an anchor (not shown) on the floor so as to keep the springs 722*a* contracted, the second transporter 5 is locked on the floor.

For example, when the springs 722*a* included in the transporter moving mechanism 722 constrain the second transporter 5 to mover vertically, the second transporter 5 is moved to recede from the caster members 721. Consequently, the transporter moving mechanism 722 introduces the caster members 721 to outside the receiving spaces of the caster receptacles 723. When the maintenance worker removes the anchor (not shown) with which the second transporter 5 is locked, the springs 722*a* stretch vertically. This permits the second transporter 5 to recede from the caster members 721.

The caster receptacles 723 are, as shown in FIG. 10, formed in the second transporter 5, and have the respective caster members 721 stored in the receiving spaces thereof. The caster receptacles 723 have a tubular shape, and the internal spaces of the caster receptacles 721 are called the receiving spaces which receive the respective caster members 721. According to the present embodiment, the receiving spaces of the caster receptacles 723 which receive the caster members 721 are formed to communicate with the spaces in the respective spring locks 722*b* included in the transporter moving mechanism 722 in which the respective springs 722*a* are stored. As mentioned above, when the second transporter 5 is moved to approach the caster members 721 by means of the transporter moving mechanism 722, the respective caster members 721 are stored in the respective receiving spaces of the caster receptacles 723.

The mark coupler 724 is formed in the second transporter 5, and coupled to a mark member 725 disposed as a mark in an installation site where the second transporter 5 is installed. According to the present embodiment, the mark coupler 724 is, as shown in FIG. 10, a concave part of the bottom of the second transporter 5 and shaped exactly like the mark member 725 so that the convex mark member 725 disposed on the floor as a mark that helps install the second transporter 5 will be fitted in the mark coupler 724. When the second transporter 5 is moved to approach the caster members 721 by means of the transport moving mechanism 722, the convex mark member 704 is coupled to the mark coupler 724. On the other hand, when the second transporter 5 is moved to recede from the caster members 721 by means of the transporter moving mechanism 722, the mark member 725 comes off from the mark coupler 724.

The installation of the second transporter 5 included in the X-ray CT system 1 in accordance with the present embodiment will be described below.

Figure 11:
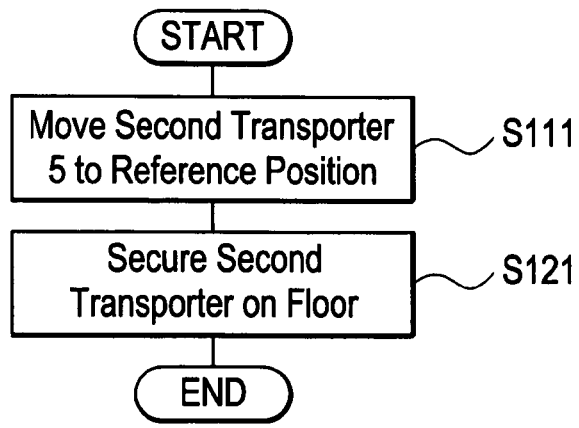
FIG. 11 is a flowchart describing actions to be performed in order to install a second transporter 5 included in the second embodiment of the present invention.

FIG. 11 is a flowchart describing actions to be performed in order to install the second transporter 5 included in the second embodiment of the present invention.

As described in FIG. 11, first, the second transporter 5 is moved to a reference position (S111).

Herein, assume that the second transporter 5 and caster members 721 are moved to recede from each other by means of the transporter moving mechanism 722. A maintenance worker horizontally presses the second transporter 5 so as to move the second transporter 5 to the reference position.

Figure 12:
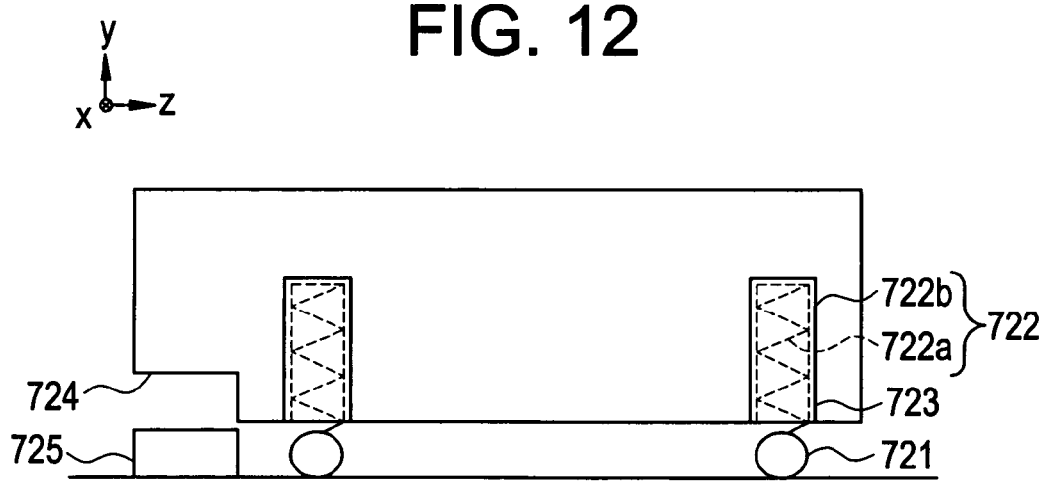
FIG. 12 is a partial side view showing the states of caster members 721, a transporter moving mechanism 722, caster receptacles 723, and a body coupler 724 attained when the second transporter 5 is moved to a reference position according to the second embodiment of the present invention.

FIG. 12 is a partial side view showing the states of the caster members 721, transporter moving mechanism 722, caster receptacles 723, and body coupler 724 attained when the second transporter 5 is moved to the reference position according to the second embodiment of the present invention.

As shown in FIG. 12, according to the present embodiment, the springs 722a included in the transporter moving mechanism 722 vertically stretch to constrain the second transporter 5 to move vertically upwards relative to the caster members 721. Consequently, the second transporter 5 is separated from the floor and borne by the wheels of the caster members 721. When the maintenance worker horizontally moves the second transporter 5 so as to rotate the wheels of the caster members 721, the second transporter 5 is moved to the reference position. In other words, when the caster members 721 get out of the respective receiving spaces of the caster receptacles 723, the second transporter 5 is moved to the reference position.

At this time, the second transporter 5 is moved while being aligned so that the convex mark member 725 disposed on the floor as a mark that helps install the second transporter 5 at the reference position will be fitted into the mark coupler 724.

Thereafter, as described in FIG. 11, the second transporter 5 is secured (S121).

Herein, the second transporter 5 and caster members 721 are moved to approach each other by means of the transporter moving mechanism 722, whereby the second transporter 5 is secured at the second position.

Figure 13:
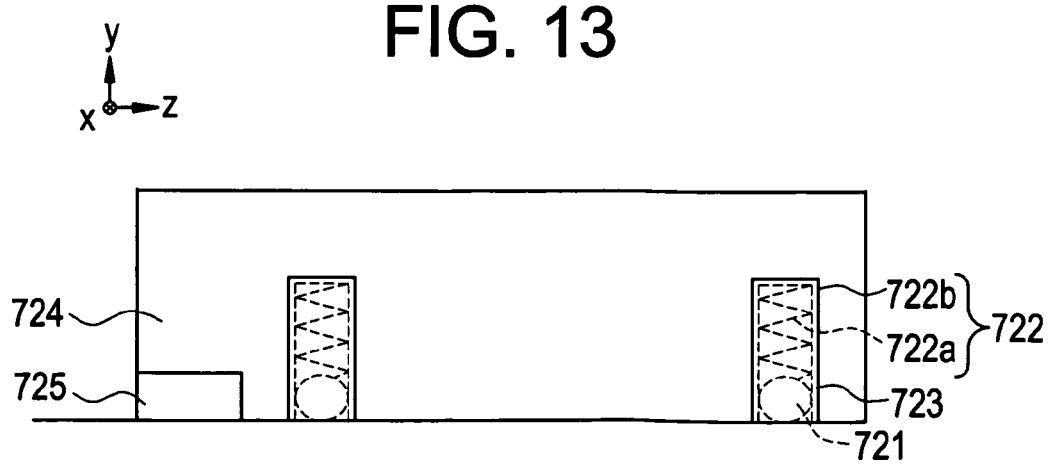
FIG. 13 is a partial side view showing the states of the caster members 721, transporter moving mechanism 722, caster receptacles 723, and body coupler 724 attained when the second transporter 5 is installed at the reference position according to the second embodiment of the present invention.

FIG. 13 is a partial side view showing the states of the caster members 721, transporter moving mechanism 722, caster receptacles 723, and body coupler 724 attained when the second transporter 5 is secured at the reference position according to the second embodiment of the present invention.

As shown in FIG. 13, according to the present embodiment, when a maintenance worker imposes a load on the second transporter 5 so as to move the second transporter 5 vertically downwards, the springs 722a included in the transporter moving mechanism 722 are vertically contracted. This causes the second transporter 5 and caster members 721 to approach each other. The caster members 721 are moved to the respective receiving spaces of the caster receptacles 723, and the convex mark member 725 is fitted into the mark coupler 724.

Thereafter, the maintenance worker places an anchor (not shown) on the floor so as to secure the second transporter 5 on the floor. Thus, the springs 722a are held contracted.

The movement of the second transporter 5 included in the X-ray CT system 1 in accordance with the present embodiment from the installed position will be described below. For example, when maintenance work is performed in order to replace a slip ring incorporated in the scanner gantry 2 with a new one, the scanner gantry 2 is uncovered. The second transporter 5 may have to be displaced from the installed position to another position in order to perform the maintenance work.

FIG. 14 is a flowchart describing actions to be performed in order to displace the second transporter 5 included in the second embodiment of the present invention from the installed position.

First, as described in FIG. 14, the second transporter 5 is separated from the floor (S211).

Herein, the second transporter 5 installed at a specific position as shown in FIG. 13 is, as shown in FIG. 12, separated from the floor so that the transporter moving mechanism 722 will recede from the respective caster members 721.

Specifically, a maintenance worker removes an anchor (not shown) with which the second transporter is secured. This causes the contracted springs 722a to stretch. Thus, the springs 722a constrain the second transporter 5 to move vertically upwards. Eventually, the second transporter 5 is separated from the floor.

Thereafter, as described in FIG. 14, the second transporter 5 is displaced from the reference position to another position (S212).

Herein, the maintenance worker presses the second transporter 5 so as to rotate the wheels of the caster members 721. Consequently, the second transporter 5 is displaced from the reference position to another position.

For example, after the maintenance work of replacing the slip ring is completed, the second transporter 5 is returned to the installed position as mentioned above.

As mentioned above, according to the present invention, the caster members 721 bear one of the components of the X-ray CT system 1 such as the second transporter 5. The transporter moving mechanism 722 included in the second transporter 5 moves the second transporter 5 vertically to the caster members 721. Herein, the transporter moving mechanism 722 moves the second transporter 5 and caster members 721 so that the second transporter 5 and caster members 721 will approach each other. Consequently, the caster members 721 are moved to the respective receiving spaces of the caster receptacles 723. When the springs included in the transporter moving mechanism 722 move the second transporter 5 and caster members 721 so that the second transporter 5 and caster members 721 will recede from each other, the caster members 721 are moved to get out of the respective receiving spaces of the caster receptacles 723.

According to the present embodiment, the second transporter 5 and caster members 721 are moved to approach each other. Consequently, the caster members 721 are moved to get out of the respective receiving spaces of the caster receptacles 723. The second transporter 5 is thus readily moved. On the other hand, when the second transporter 5 and caster members 721 are moved to recede from each other, the caster members 721 are moved to enter the respective receiving spaces of the caster members 723. The second transporter 5 can be readily installed. Consequently, according to the present embodiment, when maintenance work is performed in order to replace the slip ring incorporated in the scanner gantry 2 with a new one, or when the second transporter 5 is displaced from an installed position to another position, since the second transporter can be readily moved, the efficiency in maintenance or installation work improves. Moreover, according to the present embodiment, since the second transporter 5 can be readily installed or displaced, the freedom in laying out the components in a scan room improves.

The X-ray CT system 1 included in the aforesaid embodiments corresponds to a radiography system of the present invention. The scanner gantry 2 included in the aforesaid embodiments corresponds to a scanner included in the present invention. The X-ray tube 20 included in the aforesaid embodiments corresponds to an irradiator included in the present invention. Moreover, the X-ray detector 23 included in the aforesaid embodiments corresponds to a detector included in the present invention. Moreover, the second transporter 5 included in the aforesaid embodiments corresponds to a transfer board moving apparatus body or a component included in the present invention. Moreover, the radiographic table 401 included in the aforesaid embodiments corresponds to a radiographic table included in the present invention. Moreover, the radiographic table vertical mover 402b included in the aforesaid embodiments corresponds to a radiographic table vertical mover included in the present invention. Moreover, the radiographic table horizontal mover 402a included in the aforesaid embodiments corresponds to a radiographic table horizontal mover included in the present invention. Moreover, the intermediate table 501 included in the aforesaid embodiments corresponds to an intermediate table included in the present invention. Moreover, the rollers 501b included in the aforesaid embodiments correspond to rollers included in the present invention. The intermediate table mover 502 included in the aforesaid embodiments corresponds to an intermediate table vertical mover included in the present invention. Moreover, the stretcher coupler 503 included in the aforesaid embodiment corresponds to a stretcher coupler included in the present invention. The caster members 721 included in the aforesaid embodiment correspond to caster members included in the present invention. The transporter moving mechanism 722 included in the aforesaid embodiment corresponds to a body mover or a component mover included in the present invention. The caster receptacles 723 included in the aforesaid embodiment correspond to caster receptacles included in the present invention. Moreover, the mark coupler 724 included in the aforesaid embodiment correspond to a mark coupler included in the present invention.

The present invention is not limited to the aforesaid embodiments, but various variants may be adopted.

For example, the aforesaid embodiments are concerned with the X-ray CT systems in which the scanner gantry 2 uses X-rays to scan a subject. The present invention is not limited to this mode. For example, the present invention may be applied to a system using any other radiation such as gamma rays. Moreover, the present invention may be applied to a magnetic resonance imaging system that obtains a magnetic resonance signal induced by a subject as raw data and produces an image of the subject on the basis of the magnetic resonance signal.

In the aforesaid embodiments, the intermediate table mover 502 uses the parallel links to move the intermediate table 501 in the vertical directions V and horizontal directions H alike. The present invention is not limited to this mode. Alternatively, the present invention may be applied to a case where the intermediate table mover 502 moves the intermediate table 501 in the vertical directions V alone.

In the aforesaid embodiments, the intermediate table mover 502 moves the intermediate table 501 in a vertical direction V from the first position V1 to the second position V2. Thus, the transfer board 601 borne by the intermediate table 501 at the first position V1 is moved to the radiographic table 401 stored in the storage space S1 so that the transfer board 601 will be borne by the radiographic table 401. The present invention is not limited to this mode. Alternatively, the radiographic table vertical mover 502b may move the radiographic table 401 in a vertical direction V from the second position V2 to the first position V1. Thus, the radiographic table 401 stored in the storage space S1 at the second position V2 may be moved to the transfer board 601 borne by the intermediate table 501 at the first position V1 so that the radiographic table 401 will bear the transfer board 601. Otherwise, both the intermediate table mover 502 and radiographic table vertical mover 402b may be moved as mentioned above in order to move the transfer board 601 to the radiographic table 401.

In the aforesaid embodiment, the caster members 721 and transporter moving mechanism 722 are included in the second transporter 5. The present invention is not limited to this mode. Alternatively, the caster members 721 and transporter moving mechanism 722 may be included in the first transporter 4. Otherwise, each of components constituting a radiography system such as an X-ray CT system may be provided with the caster members 721 so that each component will be borne by the caster members. Moreover, each of the components may also be provided with a component mover similar to the transporter moving mechanism 722 so that each component can be moved vertically to the caster members 721. Likewise, each of the components may be provided with the caster receptacles and the mark coupler. The caster receptacles and mark coupler may be formed in the scanner gantry 2.

In the aforesaid embodiment, the transporter moving mechanism 722 uses the springs 722a to move the wheels of the caster members 721. The present invention is not limited to this mode. Alternatively, the transporter moving mechanism 722 may include actuators each of which is composed of a piston coupled to the wheel of each caster member 721, and a cylinder having the piston stored inside thereof, and which has the cylinders filled with a medium such as oil. In this case, the medium is supplied to the cylinders or discharged therefrom in order to vary the internal pressures of the cylinders, whereby the pistons are reciprocated. Consequently, the second transporter 5 is moved relative to the wheels of the respective caster members 721. Otherwise, an electric motor may be used to shift the position of the second transporter 5 relative to the wheels of the respective caster members 721. Otherwise, ball plungers may be used to realize both the wheels of the caster members and the capability of the transporter moving mechanism 722. Otherwise, guide rails may be laid down so that they will extend in a direction in which the wheels of the respective caster members 721 travel.

In the aforesaid embodiment, the mark member 725 has a convex shape and the mark coupler 724 has a concave shape. The present invention is not limited to this mode. Alternatively, the mark member 725 may have a concave shape and the mark coupler 724 may have a convex shape. Otherwise, the mark coupler 724 may include a ball plunger so that the ball portion of the ball plunger included in the mark coupler 724 may be fitted into the mark member 725 having a concave part.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A radiography system comprising:
   a scanner for scanning a subject in a radiographic space in order to obtain raw data of the subject, said scanner produces an image of the subject based on the raw data;
   a transfer board for supporting the subject;
   a radiographic table for moving the subject to the radiographic space while supporting said transfer board;
   an intermediate table for supporting said transfer board while transferring said transfer board between said radiographic table and a stretcher; and
   a transfer board mover for transferring said transfer board between said intermediate table and said radiographic table, wherein said radiographic table and said intermediate table are separate components.

2. The radiography system according to claim 1, wherein: said intermediate table supports said transfer board at a first position in a vertical direction, said intermediate table comprises a space in which said radiographic table is stored, said radiographic table stored at a distance from said transfer board supported at the first position, the space being formed at a second position lower than the first position; and said transfer board mover vertically moves at least one of said intermediate table and said radiographic table such that said transfer board supported by said intermediate table at the first position and said radiographic table stored in the space of said intermediate table at the second position will approach each other, thereby causing said radiographic table to support said transfer board.

3. The radiography system according to claim 2, wherein:
said transfer board mover includes an intermediate table vertical mover that vertically moves said intermediate table, said intermediate table vertical mover moves said intermediate table in a vertical direction from the first position to the second position such that said transfer board supported by said intermediate table at the first position will be moved toward said radiographic table located in the space and will be supported by said radiographic table.

4. The radiography system according to claim 2, wherein:
said transfer board mover includes a radiographic table vertical mover that vertically moves said radiographic table, said radiographic table vertical mover moves said radiographic table in a vertical direction from the second position to the first position so that said radiographic table located in the space at the second position will be moved toward said transfer board supported by said intermediate table at the first position and then will support said transfer board.

5. The radiography system according to claim 2, further comprising a radiographic table horizontal mover that horizontally moves said radiographic table toward the radiographic space, said intermediate table is located at the opposite side from which said radiographic table moves toward the radiographic space such that said radiographic table will be inserted in the space of said intermediate table by moving said radiographic table by said horizontal mover.

6. The radiography system according to claim 5, wherein:
said intermediate table further comprises a plurality of rollers that support said transfer board such that said transfer board can be horizontally moved, said plurality of rollers are oriented in a direction in which said radiographic table is moved by said radiographic table horizontal mover.

7. The radiography system according to claim 2, wherein said intermediate table further comprises rollers that support said transfer board such that said transfer board can be horizontally moved.

8. The radiography system according to claim 1, further comprising a stretcher coupler that is coupled to said stretcher supporting said transfer board.

9. The radiography system according to claim 1, wherein said scanner includes an irradiator that irradiates radiation to the subject in the radiographic space, and a detector that detects the radiation, which is irradiated from the irradiator and which transmits the subject, so as to produce raw data.

10. The radiography system according to claim 9, wherein said irradiator irradiates X-rays as the radiation.

11. The radiography system according to claim 1, further comprising:
a transfer board moving apparatus comprising said intermediate table and said transfer board mover;

caster members that support said transfer board moving apparatus, said transfer board moving apparatus further comprising an apparatus mover that moves said transfer board moving apparatus vertically to said caster members.

12. The radiography system according to claim 11, said transfer board moving apparatus further comprising caster receptacles for receiving respective caster members.

13. The radiography system according to claim 11, wherein:
said transfer board moving apparatus body further comprises a mark coupler that is coupled to a mark member formed as a mark in an installation site in which said transfer board moving apparatus body is installed.

14. A radiography system that radiographs a subject, comprising:
a plurality of radiography components comprising a radiographic table, an intermediate table, and a transfer board, said radiographic table and said intermediate table are separate components;

caster members that bear each radiography component of said plurality of radiography components, each said radiography component comprises a component mover that moves each said component vertically to said caster members.

15. The radiography system according to claim 14, each said component further comprises caster receptacles comprising receiving spaces oriented to receive a respective caster member, wherein:
when each said component and said caster members are moved to approach each other by means of said component mover, said caster members enter said respective receiving spaces of said caster receptacles; and when each said component and said caster members are moved to recede from each other by means of said component mover, said caster members are removed from said respective receiving spaces of said caster receptacles.

16. The radiography system according to claim 14, wherein:
each said component further comprises a mark coupler that is coupled to a mark member formed as a mark in an installation site in which said component is installed, wherein:

when each said component and said caster members are moved to approach each other by means of said component mover, said mark coupler and said mark member are moved to approach each other and then coupled to each other; and when each said component and said caster members are moved to recede from each other by means of said component mover, said mark coupler and said mark member are moved to recede from each other.

* * * * *